United States Patent
Kodama et al.

(10) Patent No.: US 6,797,268 B2
(45) Date of Patent: Sep. 28, 2004

(54) PHARMACEUTICAL COMPOSITION USEFUL IN THE TREATMENT OF PEPTIC ULCERS

(75) Inventors: Yoshikatsu Kodama, Gifu (JP); Nobutake Kimura, Saitama (JP)

(73) Assignees: Ghen Corporation, Gifu (JP); Nisshin Pharma Inc., Tokyo (JP)

( * ) Notice: Subject to any disclaimer, the term of this patent is extended or adjusted under 35 U.S.C. 154(b) by 12 days.

(21) Appl. No.: 09/903,734

(22) Filed: Jul. 13, 2001

(65) Prior Publication Data

US 2002/0039579 A1 Apr. 4, 2002

(30) Foreign Application Priority Data

Jul. 14, 2000 (JP) ........................................ 2000-214835

(51) Int. Cl.[7] ........................ A61K 39/40; A61K 31/44; A61K 31/425
(52) U.S. Cl. ..................... 424/157.1; 514/339; 514/371
(58) Field of Search ............................ 424/157.1, 93.4, 424/93.45; 514/339, 371

(56) References Cited

U.S. PATENT DOCUMENTS 6,419,926 B2 * 7/2002 Kodama et al. ......... 424/157.1

FOREIGN PATENT DOCUMENTS

| EP | 0 877 032 A1 | 11/1998 |
| EP | 1 010 434 A2 | 6/2000 |
| JP | 04-275232 | 9/1992 |
| JP | 10-287585 | 10/1998 |
| JP | 2001-081049 | 3/2001 |

OTHER PUBLICATIONS

Tagagi et al., Plaunotol Suppresses interleukin–8 secretion . . . , abstract, Journal o fGastroenterology and Hepatology, 2000, 15(4), 374–380.*

Romano et al., Effect of cimetidine and ranitidine on drug induced . . . , abstract, Gut. 1989, vol. 30(10), pp. 1313–1322.*

Aiba et al, "New Attempt for Inhibiting *Helicobactor pylori*", The Meeting of the 30th Japan Germ–free Animal Gnotobiology Society, Program and Abstracts (Jan., 1997) p. 22, abstract 18, with attached English language translation.

Tani et al., "Effects of anti–*Helicobactor pylori* antibodies from egg yolk antibodies on *Helicobacter pylor*", Transactions of Japan Agricultural Society (Mar., 1997) p. 52, vol. 71, abstract 20 p. 22, with attached English language translation.

Shimizu et al. "Molecular Stability of Chicken and Rabbit Immunoglobulin G," *Bioscience Biotechnology and Biochemistry*, 1992, pp. 270–274, vol. 56, No. 2, Japan Society for Bioscience, Biotechnology and Agrochemistry, Japan.

* cited by examiner

*Primary Examiner*—Vickie Kim
(74) *Attorney, Agent, or Firm*—Burns, Doane, Swecker & Mathis, LLP

(57) ABSTRACT

An inhibitor composition of *Helicobacter pylori* adhesion in the stomach comprises (1) anti-urease antibodies obtained from eggs laid by hens which have been immunized against *H. pylori* urease and (2) an inhibitor of gastric acid secretion. This inhibitor is capable of completely eliminating *H. pylori* from the stomach, so it is useful for the prevention or treatment of diseases caused by infection of *H. pylori* such as peptic ulcers.

6 Claims, 2 Drawing Sheets

PHARMACEUTICAL COMPOSITION USEFUL IN THE TREATMENT OF PEPTIC ULCERS

TECHNICAL FIELD

The present invention relates to an inhibitor of *Helicobacter pylori* adhesion and pharmaceutical compositions for oral administration useful for the effective prevention or treatment of peptic ulcers caused by *Helicobacter pylori*.

BACKGROUND OF THE INVENTION

At present it is believed that eradication of *H. pylori* from the stomach is essential for completely treating peptic ulcers. The combination of an antibiotic and an inhibitor of gastric acid secretion has been generally proposed as a therapy for eradication of *H. pylori* as described below.

*H. pylori* is a gram-negative spiral rod-shaped bacterium having flagella at one end and colonizing the human gastric mucosa. B. J. Marshall and J. R. Warren in Australia reported in 1983 that this bacterium was frequently detected in stomach biopsy specimens from patients with gastritis or gastric ulcers.

Since then, many reports have been published based on epidemiological studies, indicating that this bacterium causes gastritis, gastric ulcers, and duodenal ulcers and is associated with diseases such as gastric cancer. Once *H. pylori* colonizes gastric mucosa, it survives and persists in the stomach and cannot be eradicated, although the immune response to infection by *H. pylori* is strong, i.e., the antibody titer is high. Therefore, unless *H. pylori* is completely eliminated from the stomach by antibiotic therapy, the infection will return to the same level as before treatment within about a month after the administration of antibiotics is stopped. Additionally, the pH of the stomach is maintained very low by HCl, which is a strong acid, and therefore most antibiotics tend to be inactivated. For this reason, the combination of an antibiotic and a proton pump inhibitor which strongly suppresses the secretion of gastric acid is utilized for eradication of *H. pylori*. However, the administration of antibiotics for a long time has the serious problems of increasing antibiotic-resistant strains as well as causing side effects.

An immunological therapy approach using an oral vaccine has been proposed in order to solve problems such as side effects and the increase of antibiotic-resistant strains caused by treatment with antibiotics for the eradication of the bacteria. However, this approach has not been put to practical use. Also, an oral vaccine has problems with respect to the safety of adjutants in its practical application to humans. Additionally, the vaccine is predominantly used for prevention, and therefore it has no effect on patients who have already been infected with *H. pylori*.

As an alternative immunotherapy, the use of egg antibodies against *H. pylori* whole cell has been proposed by Aiba et al. (The Meeting of the 30th Japan Germ-free Animal Gnotobiology Society, Program and Abstracts, p22, Requested Title 18, New Attempt for Inhibiting Helicobacter pylori, January 1997), and in Japanese Patent Application Kokai No. 4-275232 and transactions of Japan Agricultural Chemistry Society, 71, p52, 20p22 (1997). However, the antibodies against *H. pylori* whole cells cannot completely eliminate *H. pylori* from the stomach, and therefore do not provide a pharmaceutical composition effective for the prevention or treatment of peptic ulcers.

SUMMARY OF THE INVENTION

It is an object of the present invention to provide a pharmaceutical composition for use in preventing or treating diseases caused by *H. pylori* such as peptic ulcers, the composition being effective and safe without the disadvantages of side effects and an increase in drug-resistant strains which are associated with the use of antibiotics.

Other objects and advantages as well as the nature of the present invention will be apparent from the following description.

Previously the present inventors obtained information with respect to *H. pylori* adhesion in the gastric mucosa, which is the key to growth thereof in the stomach, which has strong acidity, and we provided specific antibodies against *H. pylori* urease from eggs for use in completely inhibiting colonization of *H. pylori* in the gastric mucosa (Japanese Patent Application Kokai No. 10-287585). Namely, the inventors found that *H. pylori* urease participates in the colonization of *H. pylori* in gastric mucosa, and in particular that *H. pylori* urease is an adhesin, and demonstrated that antibodies against *H. pylori* urease from chicken eggs are effective for inhibiting the *H. pylori* adhesion in the gastric mucosa by binding to urease as an adhesin of *H. pylori*.

The present invention is an improvement on the above-mentioned invention, and it was made based on the discovery that the combination of the above-mentioned antibodies against *H. pylori* urease and an inhibitor of gastric acid secretion has a synergistic effect which enables a decreased dosage of the antibodies used for complete elimination of *H. pylori* from the stomach.

In one aspect, the present invention provides an inhibitor composition of *H. pylori* adhesion in the gastrointestinal tract of a mammal including humans, comprising (1) IgY antibodies obtained from at least one chicken egg laid by a hen which has been immunized with an antigenically effective amount of an isolated *Helicobacter pylori* urease, wherein said IgY antibodies are capable of specifically binding to *Helicobacter pylori* urease in the gastrointestinal tract of the mammal, and (2) an inhibitor of gastric acid secretion.

In another aspect, the present invention provides a pharmaceutical composition for preventing and/or treating a disease caused by or associated with *Helicobacter pylori* in a mammal including humans, comprising a pharmaceutically effective amount of the inhibitor composition comprising (1) IgY antibodies obtained from at least one chicken egg laid by a hen which has been immunized with an antigenically effective amount of an isolated *Helicobacter pylori* urease, wherein said IgY antibodies are capable of specifically binding to *Helicobacter pylori* urease in the gastrointestinal tract of the mammal, and (2) an inhibitor of gastric acid secretion, and a pharmaceutically acceptable carrier or diluent.

DESCRIPTION OF THE PREFERRED EMBODIMENTS

Figure 1:
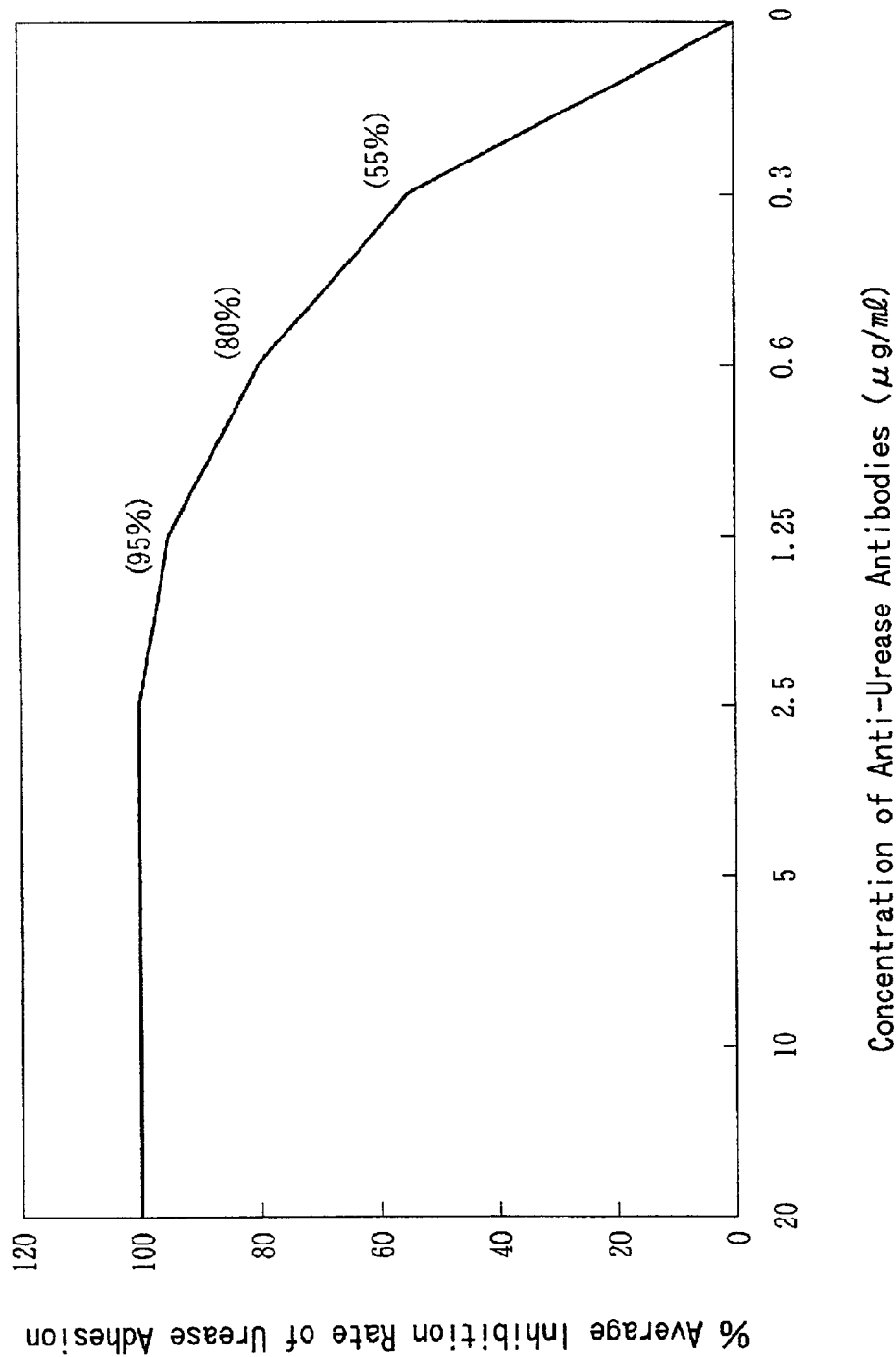
FIG. 1 is a graph showing the inhibition rate of *H. pylori* urease adhesion when using anti-urease antibodies from eggs.

In order to produce the specific antibodies used in the present invention, hens are immunized against an antigen. As an antigen to immunize hens, urease of *H. pylori* is prepared. *H. pylori* strains to be used for preparation of an antigen include human clinical isolates such as #130(Cag A+)(Vac A+), NSP#305(Cag A+)(Vac A+), NSP#335(Cag A+)(Vac A+), NSP#355(Cag A−)(Vac A−). After culturing a selected strain, a urease antigen is prepared by an appropriate method such as affinity column chromatography using Cellulofine sulfate gel (J.Biol.Chem.,273:18130–18138, 1998).

As a urease antigen, recombinant urease may be used. Recombinant urease may be prepared in a conventional way. For example, genomic DNA of *H. pylori* can be extracted, and a gene coding urease molecule can be amplified by the PCR method to obtain amplified DNA, which can be subsequently integrated into an expression vector for *E. coli* (e.g. pKK233-2) by a known method. The obtained vector can be incorporated into a suitable host, *E.coli* (e.g. *E.coli* XL1-Blue) to produce recombinants. The recombinants can be cultured in a suitable culture medium, thereby expressing urease. Recombinant urease can be obtained by recovering the expressed urease. In preparing recombinant urease, expression systems using yeasts, mammal cells and insect cells may be used. Procedures for preparing recombinant urease are described in detail, for example, in Molecular Cloning, Laboratory Manual (2nd ed.) (Cold Spring Harbor Press), and in DNA Cloning 2 (2nd ed.) (IRL Press).

The immunization of hens against an antigen may be performed by inoculation with the antigen by an appropriate route such as subcutaneous or intramuscular injection. Preferably a suitable adjuvant is administered in conjunction with the antigen to enhance the immunization. Adjuvants useful for this purpose are Freund's complete (incomplete) adjuvant (Difco), Cholera toxin BB (Sigma), Titer Max (CytRx Corp.) etc.

The dose of the antigen is determined based on the type of antigen and adjuvant and the administration route in such a manner that an immune state is induced in the hen without producing excessive toxicity of the antigen therein. Usually, within a few weeks after the inoculation (initial immunization), the hen becomes sensitive to the antigen, i.e., immunized against the antigen. Specific antibodies against the antigen are produced within the body of the hen, and eggs laid by the hen, especially the yolks of the eggs, contain the specific antibodies.

Immunization may be performed by several inoculations with an antigen. Also, after the initial immunization of the hen against the antigen, one or more boosters at an appropriate dose level may be administered in order to maintain a high antibody titer in the hen.

The presence and titer level of the specific antibodies against the antigen in the hen and in eggs of the hen can be confirmed by any method known to those skilled in the art of immunological assays, such as ELISA or a method using agglutination reaction.

After it is confirmed that an adequate titer of the specific antibodies is present in eggs laid by the immunized hen, eggs laid by the hen are collected and the desired antibodies are recovered.

The specific antibodies used in the present invention may be prepared from the overall ovum or the yolk of the eggs. Most antibodies are contained in the yolk of an egg, and usually the yolk is separated from the egg for use in the production of the antibodies. In some cases, the overall ovum of the egg may be used.

The overall ovum or the yolk of the egg containing the desired antibodies may be used without fractionation. Alternatively, the overall ovum or the yolk of the egg may be subjected to fractionation or purification. For example, a delipidization procedure may be carried out by suitable methods such as methods using hydroxypropyl methycellurose phthalate, polyethylene glycol, etc. to remove lipid components from the yolk. If desired, further purification may be carried out by any known method, including known purification procedures of proteins such as salting out with ammonium sulfate or sodium sulfate or cold ethanol precipitation, etc.

The overall ovum or the yolk of the egg, without fractionation or with fractionation or purification, may be used directly, or it may be processed. In a preferred embodiment, the overall ovum or the yolk may be stirred or homogenized into an emulsion and dried to form a powder by conventional techniques such as spray drying or lyophilizing. Thus, various forms of antibodies may be used, depending on the purpose.

Examples of the inhibitor of gastric acid secretion used in the present invention include $H_2$ blockers such as famotidine, nizatidine, roxatidine, ranitidine or cimetidine and proton pump inhibitors such as omeprazol, lansoprazol or sodium rabeprazole.

The inhibitor of the present invention can completely eliminate *H. pylori* which has been adhered to gastric mucosa from the stomach in *H. pylori*-infected animal model. This effect is attained even with a small amount of the specific antibodies from eggs contained in the inhibitor of the present invention. For example, as shown in Experiment 2, the elimination rate is 90% when the specific antibodies are administered alone to mice at a concentration of 0.0025% in feed. However, the combination with an inhibitor of gastric acid secretion enables an elimination rate of 100% even at a concentration of 0.0025% of the antibodies in feed. When the elimination rate is 90%, the infection will return to the same level as before the treatment if the administration is stopped. Therefore, an elimination rate of 100% is desired for a pharmaceutical composition for treatment of peptic ulcers. For an elimination rate of 100%, 0.25% of the antibodies in feed is necessary when the antibodies alone are administered, but only 0.0025% of the antibodies is necessary when administered along with an inhibitor of gastric acid secretion in feed. Thus, one-hundredth the amount of antibodies is enough to completely eliminate *H. pylori* from the stomach compared with when the antibodies alone are administered. Thus, according to the present invention, a remarkably decreased dose of the antibodies can completely eradicate *H. pylori* in the stomach. The administration of an inhibitor of gastric acid secretion alone does not show an effect on the decrease of the number of *H. pylori* cells colonized in the stomach. Therefore, the composition of the present invention has a synergistic effect.

With respect to the prior art combination of an antibiotic and an inhibitor of gastric acid secretion, it is said that an inhibitor of gastric acid secretion prevents an antibiotic from deterioration due to hydrochloric acid (gastric acid) and that an antibiotic acts directly on *H. pylori* cells. The mechanism of the specific antibodies used in the present invention is different from that of an antibiotic. The antibodies specific for *H. pylori* urease bind to urease, an adhesin of *H. pylori*, to form macro aggregates by crosslinking between antigens (urease) and antibodies, leading to a decrease in the colonization ability of *H. pylori*. This process may be promoted by the use of an inhibitor of gastric acid secretion. The inhibitor of *H. pylori* colonization of the present invention can be used as a safe, effective, and inexpensive pharmaceutical composition suitable for preventing or treating diseases caused by or associated with *H. pylori* such as peptic ulcers.

The inhibitor of the present invention can be used alone or along with conventional additives as a pharmaceutical composition for prevention or treatment of peptic ulcers, etc. The inhibitor alone or along with additives may be formed by a conventional method into a preparation for oral administration such as tablets, granules, powders, capsules or liquid preparations. The additives which may be used include excipients, binders, disintegrators, lubricants, antioxidants, coloring materials, corrigents, and the like.

Excipients which can be used in a pharmaceutical composition include sodium carboxymethylcellulose, agar, light anhydrous silicic acid, gelatin, crystalline cellulose, sorbitol, talc, dextrin, starch, lactose, sucrose, glucose, mannitol, magnesium metasilicate aluminate, calcium hydrogen phosphate, and the like.

Binders which can be used include gum arabic, sodium alginate, ethanol, ethyl cellulose, sodium caseinate, sodium carboxymethylcellulose, agar, purified water, gelatin, starch, tragacanth, lactose, hydroxycellulose, hydroxymethycellulose, hydroxypropyl cellulose, polyvinylpyrrolidon, and the like.

Disintegrators which can be used include carboxymethylcellulose, sodium carboxymethylcellulose, calcium carboxymethylcellulose, crystalline cellulose, starch, hydroxypropyl starch, and the like.

Lubricants which can be used include stearic acid, calcium stearate, magnesium stearate, talc, hydrogenated oil, sucrose fatty acid ester, wax, and the like.

Antioxidants which can be used include tocopherol, gallic acid ester, dibutyl hydroxy toluene (BHT), butyl hydroxy anisol (BHA), ascorbic acid, and the like.

Other additional additives or agents may be added if desired, such as antacids (e.g., sodium hydrogen carbonate, magnesium carbonate, precipitated calcium carbonate, synthetic hydrotalsite), agents for protection of gastric mucosa (e.g., synthetic aluminum silicate, sucralfate, and sodium copper chlorophyllin) and digestive enzymes (e.g., biodiastase or lipase).

The administration of a pharmaceutical composition for prevention or treatment of peptic ulcers, etc. may be by an oral route. The dosage of the antibodies in the composition of the present invention will be usually 0.5–20 mg and preferably 2–15 mg (as purified antibodies) per day for an adult. The dosage of the inhibitor of gastric acid secretion is preferably 20–30 mg per day for an adult.

The following examples are given to further illustrate the present invention. It should be understood that the present invention is not limited to the specific details set forth in the examples.

EXAMPLE 1

(1) Preparation of Recombinant Urease of *H. pylori*

Genomic DNA of *H. pylori* strainTU130 was extracted, and the DNA coding urease molecule was amplified by the PCR method. The amplified DNA was integrated into expression vector pKK233-2 (Pharmacia) to obtain vectors to be used for expressing urease. The vector was incorporated into *E. coli* XL 1-Blue to obtain *E. coli* capable of expressing urease. The recombinant bacteria were cultured with shaking at 100 rpm at 37° C. in 1.0 liter of LB medium containing 100 $\mu$g/ml of ampicillin. When the bacterial cells reached a logarithmic growth phase, isopropyl-$\beta$-D-thiogalactopyranoside (IPTG) was added at a concentration of 0.5 mM in order to induce expression, and the cells were further cultured with shaking overnight under the same conditions as above. The *E. coli* cells were harvested by centrifugation at 4,000×g for 20 minutes (+4° C.).

The obtained cells were suspended in tris buffer for lysis (50 mM Tris-HCl (pH 8.0), 100 mM NaCl, 1 mM EDTA). After addition of lysozyme at a concentration of 0.1 mg/ml, the suspension was allowed to stand in ice for 30 minutes. Then, the suspension was frozen at −80° C. for more than 1 hour and was thawed at room temperature. The suspension was treated by ultrasonic waves, and Triton X-100 was added at a concentration of 1%. Inclusion bodies of recombinant urease were collected by centrifugation at 30,000×g for 30 minutes (+4° C.),.

These inclusion bodies were suspended in a buffer for washing inclusion bodies (50 mM Tris-HCl (pH 8.0), 150 mM NaCl, 1 mM EDTA containing 0.1% SDS, 1.0% Triton X-100, 1.0% sodium deoxycholate) and centrifuged at 30,000×g for 20 minutes (+4° C.). The precipitated inclusion bodies were further washed twice in the same manner. The resulting inclusion bodies were diluted with PBS so as to be used as an antigen for immunization.

The obtained recombinant urease were confirmed to be the same as natural urease of *H. pylori* by SDS-PAGE and western blotting.

(2) Immunization of Hens

Immunization was carried out using white Leghorn, strain Hyline W36 hens about 12 weeks old. The antigen for immunization obtained in (1) described above (adjusted to contain 0.5 mg/ml of protein) was mixed with an oily adjuvant and was injected into the right and left pectoral muscles at a dose of 0.5 ml per injection (initial immunization). Six weeks after the initial immunization, the same antigen was injected as a booster in the same manner and at the same dose. The antibody titer of the egg yolk of eggs laid by these immunized hens increased significantly and became stable. About two weeks after the booster injection, the collection of the eggs was begun and continued for four weeks. The antibody titer of the egg yolk of the eggs was stable for 4–6 months. After that, the antibody titer decreased, and then the injection was repeated using the same procedure as described above to restore the titer.

(3) Assay of the antibody titer of egg yolk

The yolk was separated from the albumen of each egg and weighed. To this yolk, an equal volume of PBS was added to dissolve the yolk component. To this mixture, an equal volume of chloroform was added, and then the mixture was vigorously stirred with shaking. After being allowed to stand at 37° C. for 15 minutes, the mixture was centrifuged. The obtained supernatant was used as a sample for determining the antibody titer. The antibody titer of supernatant was determined by ELISA. The ELISA procedure was as follows. The optimum concentration of immobilized antigen and a conjugate of horseradish peroxidase-anti-fowl IgG was determined by checkerboard titration. A 96-well plate was used as a plate and native urease of *H. pylori* and solubilized *H. pylori* whole cell antigen was used for immobilizing. Antigens were diluted with carbonate buffer (pH 9.6) so as to contain 5 $\mu$g/ml of protein, and 100 $\mu$l of the diluted antigen was put into each well and was allowed to stand overnight at 4° C.

After each well was washed three times with PBS-Tween 20, 150 $\mu$l of 3% BSA solution was added for blocking, and each well was allowed to stand at 37° C. for 60 minutes. Then, each well was washed three times with PBS-Tween 20, and 100 $\mu$l of each sample was added to each well to react at 37° C. for 60 minutes. After reaction, the well was washed with PBS-Tween 20 and 12,000-fold diluted conjugate was added in an amount of 100 $\mu$l/well to react at 37° C. for 60 minutes. After each well was washed five times, a substrate (o-phenylenediamine 2 hydrochloride containing $H_2O_2$) was added to the well to produce color at room temperature. After 20 minutes, 50 $\mu$l/well of 3N $H_2SO_4$ was added to stop the reaction. Then, absorbance at 490 nm in each well was measured by an ELISA autoreader. Two-fold serially diluted egg yolk antibodies against urease having a known titer were placed in a running plate. The antibody titer of the sample was determined from the resulting calibration curve.

(4) Preparation of Antibodies from Egg Yolk

After the immunized eggs were washed and disinfected, the yolk was separated from the albumen of each egg, and combined yolk from a plurality of eggs was divided into groups of 8 kg and stored below −20° C. until used. The purification procedures were as follows. To 7.5 kg of the yolk as a starting material was added a 10-fold amount (by weight) of distilled water to delipidize. To the supernatant was added ammonium sulfate to produce 40% saturation. The mixture was stirred and centrifuged to obtain pellets. The pellets were dissolved in saline, and 30% saturation salting out was carried out to obtain pellets. The obtained pellets were dissolved in a small amount of saline, and to this mixture ethanol at −20° C. was added with stirring so as to give a final concentration of 50%. After centrifugation, the pellets were dissolved in saline and lyophilized. As a result, 11 g of pale yellowish white powder were obtained. The recovery rate of antibodies was about 47%, the purity of IgG was not less than 95%, and the water content was not more than 2%.

Experiment 1 in Vitro Experiment

Using the egg yolk antibodies against urease prepared as described above in Example 1 (4), the inhibitory effects thereof on H. pylori urease adhesion to gastric mucosa were examined by in vitro experiments.

Materials and Methods

The present inventors had already found that an adhesin of H. pylori is urease produced by H. pylori. Since this urease binds to mucin of gastric mucosa, porcine gastric mucin was used for an inhibition test of urease adhesion.

Preparation of Porcine Gastric Mucin

Healthy pigs about two months old were slaughtered, and their stomachs were recovered and washed on the insides thereof with 0.1M phosphate buffer (pH 7.4) containing 0.15M NaCl, 5 mM N-ethyl maleimide (NEM), 1 mM phenylmethylsulfonyl fluoride (PMSF) and 1 mM EDTA. The stomachs were incised, and gastric mucosa was scraped and suspended in the above-mentioned buffer. This suspension of mucosa was homogenized by a Polytron homogenizer while being iced and was centrifuged at 15,000×g to recover supernatant. The supernatant was centrifuged again at 25,000×g to recover supernatant, which was dialyzed against distilled water and lyophilized to obtain crude gastric mucin. Then, this lyophilized crude gastric mucin was dissolved in PBS (pH 6.8) containing 6M guanidine hydrochloride and protease inhibitor (5 mM NEM, 1 mM PMSF, 1 mM EDTA), and overlaid on a cesium chloride density gradient (1.5 g/ml) and centrifuged at 200,000×g for 48 hours. A sialic acid-containing fraction was detected by nitrocellulose membrane blotting and dyeing with periodic acid Schiff's reagent. Dyed fractions were pooled and overlaid on a cesium chloride density gradient and centrifuged. Dyeing-positive fractions were pooled and lyophilized. Then, the lyophilized product was subjected to gel filtration through a Sepharose CL-4B column preequilibrated with a 0.1M phosphate buffer (0.1M NaCl, pH 6.8) to carry out fractionation. Fractions which were PAS dyeing-positive and had proteins at a high concentration were pooled and dialyzed against PBS (pH 6.8) to obtain purified porcine gastric mucin, which was stored at −80° C. until use. The obtained purified gastric mucin was confirmed to be glycoprotein of 66 kD by SDS-PAGE.

Inhibition Test of Urease Adhesion

A microplate for a urease adhesion test was prepared as follows.

To each well of a 96-well microplate, a 50 μl portion of native urease (5.0 μg/ml) was added, and was subjected to immobilization by being left to stand overnight at 4° C. When the microplate is used, blocking is conducted by adding 3% BSA to each well to react at 37° C. for 60 minutes, and then the plate is washed three times with an adhesion medium (20 mM phosphate buffer containing 0.05% Tween 20 and 0.15M NaCl).

Inhibition tests of urease adhesion were conducted using the microplate prepared above as follows. First, samples having various concentrations were each mixed with biotinylated porcine gastric mucin, and each mixture was transferred to each well of a 96-well microplate immobilized with urease, and the plate was sensitized at 37° C. for 60 minutes. Then, each well in the microplate was washed five times with adhesion medium (pH 4.0) and was fixed by heating at 65° C. for 10 minutes. The fixed wells were washed once with an adhesion medium (pH 7.0), and HRP-streptoavidin was added to each well to react at room temperature for 30 minutes in order to detect biotinylated porcine gastric mucin adhered to urease. Then, a substrate (orthophenylenediamine 2HCl and $H_2O_2$) was added to react. 3N $H_2SO_4$ was used for termination of the reaction. Then, absorbance at 490 nm in each well was measured by an ELISA autoreader. Known amounts of porcine gastric mucin were diluted serially 2-fold and placed in a running plate, and a calibration curve thereof was used to determine the amount of porcine gastric mucin in a sample.

Results

Inhibition of Urease Adhesion with Anti-urease Antibodies from Egg Yolk

As shown in FIG. 1, urease adhesion to porcine gastric mucin was inhibited dose-dependently with anti-urease antibodies from egg yolk. Urease is localized on the surface of Hp cells, and therefore the anti-urease antibodies can inhibit infection with H. pylori, i.e., it can eliminate H. pylori from the stomach, by binding to urease of the cells and masking urease, an adhesin, in the stomach.

The inhibition rate of urease adhesion was almost 100% at a concentration of more than 2.5 μg/ml of the anti-urease antibodies from egg yolk, and it decreased to half this level at a concentration of 0.25 μg/ml.

Experiment 2 In Vivo Experiment

This experiment was performed in an animal model to demonstrate the synergistic effects of the combination of the egg yolk anti-urease antibodies prepared in Example 1 and an inhibitor of gastric acid secretion on H. pylori elimination.

Method

The experimental animal was a hairless mouse (NS:Hr/ICR, Research Institute for Human and Animal Propagation, Accession No. IAR-NHI-9701) (ATCC #72024) (Clin. Diagn. Lab. Immunol. 5: 578–582, 1998) having a high sensitivity to H. pylori infection. Each mouse was challenged with 1×10$^6$ CFU of strain NSP 335 by oral administration. After breeding for a week, the mice were administered a feed containing the egg yolk antibodies against urease at various concentrations and an $H_2$ blocker (famotidine) or proton pump inhibitor (omeprazol) at a concentration of 1 mg/mouse/day for 4 weeks. A control group was administered a feed containing no antibodies and $H_2$ blocker or proton pump inhibitor. There were 10 mice in each group. After the completion of administration, the mice in each group were slaughtered. The stomachs of the mice were recovered, and after removal of the contents, the whole mucous membrane was homogenized by a homogenizer to form an emulsion, which was used for detection of H. pylori. The detection of H. pylori was carried out by placing the emulsion on a medium for detecting H. pylori (Poremedia H. pylori isolation medium, Eiken Kagaku), incubating at 37° C. for 5 days by the gas pack method, and counting colonies.

Results

Figure 2:
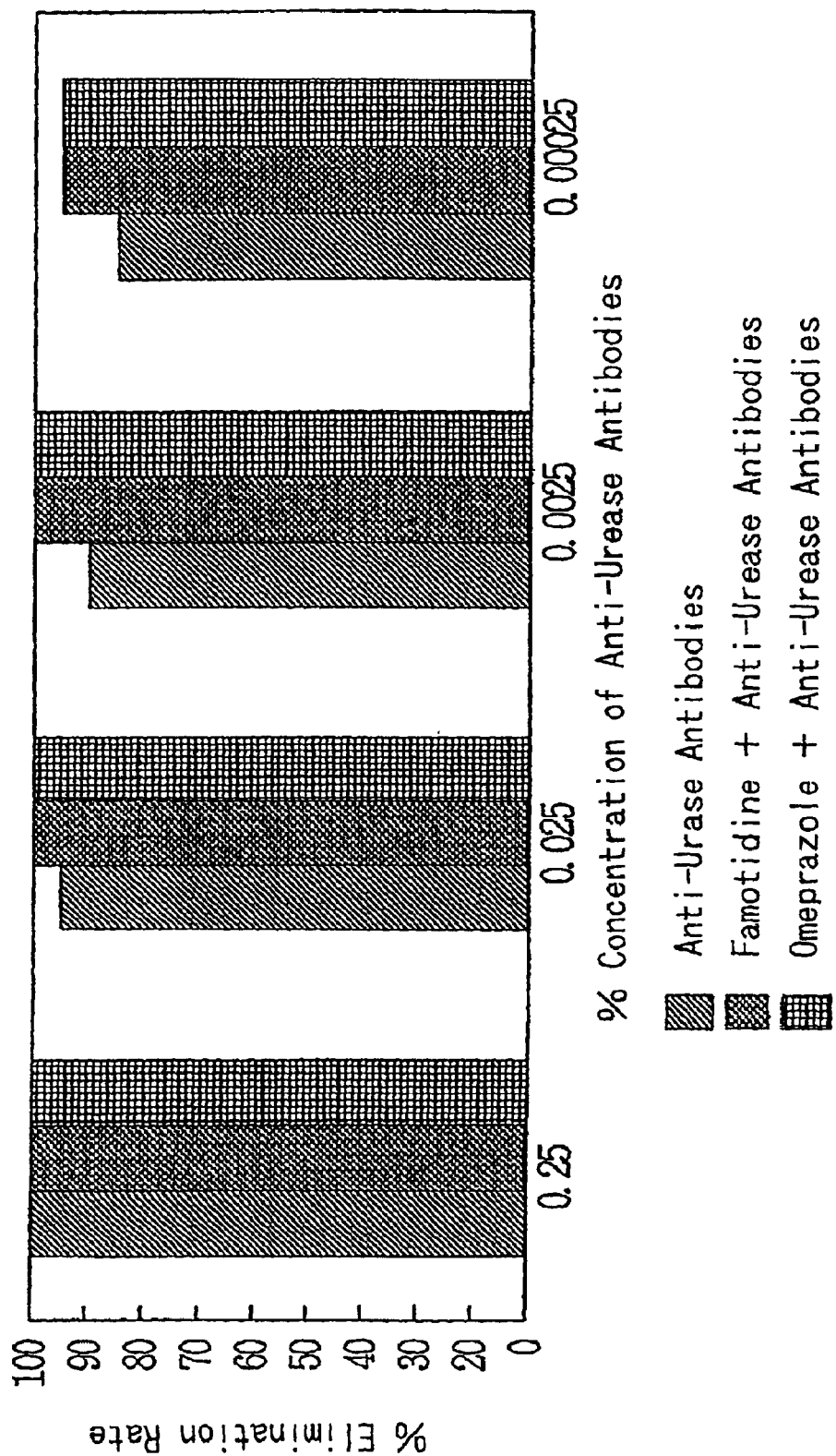
FIG. 2 is a graph showing the elimination rate of *H. pylori* in *H. pylori* colonized mice.

Effects of the Combination of the Anti-urease Antibodies and an Inhibitor of Gastric Acid Secretion on Elimination of H. pylori in H. pylori-colonized Mice As shown in FIG. 2, the anti-urease antibodies from egg yolk could eliminate H. pylori from the stomach in a concentration-dependent manner. An elimination rate of 100% was achieved at an antibody concentration in feed of 0.25%. An antibody concentration in feed of 0.0025% could achieve an elimination rate of 90%, which is not adequate for treatment of peptic ulcers. However, the combination of the antibodies with an inhibitor of gastric acid secretion enabled an elimination rate of 100% at an antibody concentration in the feed of 0.0025%. This means that antibodies can completely eliminate *H. pylori* from the stomach of *H. pylori*-colonized mice in combination with an inhibitor of gastric acid secretion at even one-hundredth of the level required when the antibodies are used alone. 100% of mice (10/10) in the control group were infected with *H. pylori*.

PREPARATION EXAMPLE 1

Below, examples of various pharmaceutical compositions for peptic ulcers are given. The anti-urease antibodies from eggs used in the examples are the anti-unrease antibodies prepared by Example 1.

Formula 1: in 1.5 kg of Fine Particles

| | | |
|---|---|---|
| anti-urease antibodies | 10 g |
| famotidine | 20 g |
| lactose | 1,100 g |
| corn starch | 320 g |
| PVP (K-30) | 50 g |

These components were granulated by a wet granulation method, followed by drying and forming into fine particles in a conventional way.

Formula 2: Tablets

| | | |
|---|---|---|
| 1. | anti-urease antibodies | 10 g |
| 2. | famotidine | 30 g |
| 3. | lactose | 400 g |
| 4. | corn starch | 125 g |
| 5. | crystalline cellulose | 210 g |
| 6. | PVP (K-300) | 25 g |
| 7. | magnesium stearate | 10 g |

The above components 1–6 were formulated into granules by a wet granulation method, magnesium stearate was then added to form powder for preparing tablets, and then the powder was compressed into tablets (200 mg/tablet).

Formula 3: in 1.5 kg of Granules

| | | |
|---|---|---|
| anti-urease antibodies | 15 g |
| famotidine | 30 g |
| lactose (200M) | 950 g |
| corn starch | 450 g |
| PVP (K-30) | 50 g |

These components were granulated by an extrusion granulation method, followed by drying and forming into granules in a conventional way.

As is apparent from the above, in accordance with the present invention, the combination of anti-urease antibodies from eggs and an inhibitor of gastric acid secretion can eliminate *H. pylori* completely from the stomach, even when a small amount of the anti-urease antibodies is used.

Therefore, a safe, effective and inexpensive pharmaceutical composition for prevention or treatment of peptic ulcers caused by *H. pylori* infection is provided.

What is claimed is:

1. A synergistic inhibitor composition of *Helicobacter pylori* adhesion in the gastrointestinal tract of a mammal, consisting essentially of (1) IgY antibodies obtained from at least one chicken egg laid by a hen which has been immunized with an antigenically effective amount of an isolated *Helicobacter pylori* urease, wherein said IgY antibodies are capable of specifically binding to the adhesion portion of *Helicobacter pylori* urease in the gastrointestinal tract of the mammal, and (2) at least one agent selected from $H_2$ blockers and proton pump inhibitors.

2. The inhibitor composition according to claim 1, wherein the IgY antibodies are isolated and purified antibodies.

3. A pharmaceutical composition for preventing and/or treating a disease caused by or associated with *Helicobacier pylori* in a mammal, consisting essentially of:

a pharmaceutically effective amount of a synergistic inhibitor composition consisting essentially of (1) IgY antibodies obtained from at least one chicken egg laid by a hen which has been immunized with an antigenically effective amount of an isolated *Helicobacter pylori* urease, wherein said IgY antibodies are capable of specifically binding to the adhesion portion of *Helicobacter pylori* urease in the gastrointestinal tract of the mammal, and (2) at least one agent selected from $H_2$ blockers and proton pump inhibitors; and a pharmaceutically acceptable carrier or diluent.

4. The pharmaceutical composition according to claim 3, wherein the IgY antibodies are isolated and purified antibodies.

5. The inhibitor composition according to claim 1, wherein the mammal is a human.

6. The pharmaceutical composition according to claim 3, wherein the mammal is a human.

* * * * *